(12) United States Patent
Savage et al.

(10) Patent No.: US 11,513,114 B2
(45) Date of Patent: Nov. 29, 2022

(54) KILL EVENT OPTIMIZATION

(71) Applicant: ABS Global, Inc., DeForest, WI (US)

(72) Inventors: Frederick Savage, DeForest, WI (US);
Matthew Ebersole, DeForest, WI (US);
Daniel McAda, DeForest, WI (US);
David Appleyard, DeForest, WI (US);
Zheng Xia, DeForest, WI (US)

(73) Assignee: ABS Global, Inc., DeForest, WI (US)

( * ) Notice: Subject to any disclaimer, the term of this patent is extended or adjusted under 35 U.S.C. 154(b) by 300 days.

(21) Appl. No.: 15/929,938

(22) Filed: May 29, 2020

(65) Prior Publication Data
US 2020/0378953 A1 Dec. 3, 2020

Related U.S. Application Data

(60) Provisional application No. 62/854,163, filed on May 29, 2019.

(51) Int. Cl.
*G01N 33/50* (2006.01)
*G01N 21/64* (2006.01)

(52) U.S. Cl.
CPC ..... *G01N 33/5091* (2013.01); *G01N 21/6456* (2013.01); *G01N 21/6486* (2013.01)

(58) Field of Classification Search
CPC ........... G01N 21/6456; G01N 21/6486; G01N 33/5091
See application file for complete search history.

(56) References Cited

U.S. PATENT DOCUMENTS

| | | | |
|---|---|---|---|
| 5,135,759 A | 8/1992 | Johnson | |
| 5,541,081 A * | 7/1996 | Hardy | G01N 33/5091 435/25 |
| 5,700,692 A | 12/1997 | Sweet | |
| 7,629,113 B2 * | 12/2009 | Seidel | A01K 67/027 800/15 |
| 7,713,687 B2 * | 5/2010 | Seidel | A01N 1/0226 435/6.19 |
| 7,723,116 B2 * | 5/2010 | Evans | G01N 15/147 436/63 |
| 7,758,811 B2 * | 7/2010 | Durack | A01N 1/0284 436/63 |
| 7,820,425 B2 * | 10/2010 | Schenk | A01N 1/02 435/325 |
| 8,941,062 B2 | 1/2015 | Wagner et al. | |
| 2002/0018211 A1 * | 2/2002 | Megerle | G01N 15/1456 356/440 |

(Continued)

*Primary Examiner* — Blake C Riddick
(74) *Attorney, Agent, or Firm* — McKee, Voorhees & Sease, PLC (57) ABSTRACT

A method of choosing which undesired cell to destroy in a multi-cell fluorescent event includes detecting fluorescence of cells, converting photons detected in the fluorescence into an analog voltage output signal, and identifying at least two discernable peaks associated with the cells. By looking solely at properties measured within the multi-cell fluorescent event, a decision of which cell to target for elimination can be made. Using this method with large population sizes can result in an effective sex skewed product. The sex skewed product can, for example, be formed from bull semen which is then later used to inseminate cows which results in an increased likelihood of giving birth to female cattle.

20 Claims, 6 Drawing Sheets

(56) References Cited

U.S. PATENT DOCUMENTS

| | | | | |
|---|---|---|---|---|
| 2003/0135876 A1* | 7/2003 | Mobraaten | ........... | C12N 5/0609 800/21 |
| 2009/0142765 A1* | 6/2009 | Vacca | ................ | G01N 15/1425 435/6.12 |
| 2012/0122084 A1* | 5/2012 | Wagner | ................ | G01N 15/147 435/6.1 |
| 2019/0187043 A1* | 6/2019 | Wagner | .............. | G01N 15/1475 |

* cited by examiner

KILL EVENT OPTIMIZATION

CROSS-REFERENCE TO RELATED APPLICATIONS

This application claims priority under 35 U.S.C. § 119 to provisional application Ser. No. 62/854,163, filed May 29, 2019, herein incorporated by reference in its entirety.

FIELD OF THE INVENTION

The present disclosure relates generally to optimizing scientific instrumentation responsible for the sexation of sperm cells using single event relationship statistics. More particularly, the present disclosure relates to optimizing an apparatus and method to increase throughput and/or yield by particularly identifying and targeting specific events for sorting, and/or precluding specific events from sorting.

BACKGROUND OF THE INVENTION

The background description provided herein is for the purpose of generally presenting the context of the present disclosure. Work of the presently named inventors, to the extent the work is described in the present disclosure, as well as aspects of the description that may not otherwise qualify as prior art at the time of filing, are neither expressly nor impliedly admitted as prior art.

Sexed semen (i.e. semen samples wherein the intact, fertile sperm cells are predominantly either X-chromosome bearing or Y-chromosome bearing) is important in a number of applications and industries. High purity sperm cell populations that have been differentiated based on chromosomal differences—such as, for example, sperm cell populations that are skewed toward X-chromosome bearing or Y-chromosome bearing populations of spermatozoa, rather than the naturally-occurring 50:50 X:Y chromosome split—can be utilized to accomplish in vitro or in vivo fertilization, including artificial insemination (AI) or in vitro fertilization (IVF) of ova or oocytes of numerous mammals such as bovids, equids, ovids, goats, swine, dogs, cats, camels, elephants, oxen, buffalo, or the like. See, e.g., U.S. Pat. No. 5,135,759.

The most common method for sexing sperm cells is to discriminate based on DNA content. In this context, sperm is combined with an extender and a luminescent dye to stain the DNA inside the sperm cell. The stained sperm cells are then placed in a sample fluid which is introduced into a channel of a microfluidic chip that uses focusing techniques to orient the sperm cell into a substantially single-file stream. After being properly oriented, the sperm cells are illuminated with a light source (e.g., a laser), which excites the luminescent dye in the DNA, giving off a fluorescent luminescence which is detected by a detector (e.g., a photomultiplier tube (PMT), an avalanche photodiode (APD), or a silicon photomultiplier (SiPMD)). A sperm containing the X chromosome has more DNA than a Y chromosome-bearing sperm, resulting in the X chromosome-bearing sperm producing more luminescence in response to the detection light source. The detected luminescence is monitored and the system takes selective action, e.g., sorting or killing non-selected sexed sperm with a kill laser, on the individual sperm cells to achieve an end product with the desired characteristics, e.g., a sample with high concentration of either X or Y chromosome-bearing sperm. For example, if female calves are desired (e.g., for dairy production), then the system is calibrated to collect cells having detected luminescence parameters that are what would be expected of an X chromosome-bearing sperm cell. Alternatively, if male calves are desired (e.g., for beef production), then the system is calibrated to collect cells having detected luminescence parameters that are what would be expected of a Y chromosome-bearing sperm cell.

Sperm cells may also be distinguished based on DNA content by other methods that do not utilize a DNA dye. For example, U.S. Pat. No. 8,941,062 describes systems and methods of cytometry involving presenting a single sperm cell to at least one laser source configured to deliver light to the sperm cell in order to induce bond vibrations in the sperm cell DNA and detecting the signature of the bond vibrations. Sperm cells may also be analyzed and distinguished based on the presence or absence of cell surface markers or protein, through binding of a fluorescently labeled ligand, such as an antibody. Other methods for discriminating sperm cells may utilize other features of sperm cells, such as mass or volume, to differentiate between those that contain X-chromosomes and those that contain Y-chromosomes. These discrimination and detection methods similarly permit the cells to be selectively differentiated and for the sample to be sexed.

Sexing techniques include a variety of methods to sort, separate, eliminate, destroy, or inactivate unwanted cells. For example, so-called laser kill methods involve exposure of particular cells to a laser with sufficient energy to inactivate the cells. Cells may also be separated into populations through sorting, for example through droplet formation and deflection as described in U.S. Pat. No. 5,700,692. Other techniques that may be implemented for sexing include piezoelectric actuation, dielectrophoresis of droplets, electrolysis or electroporation, optical manipulation (optical trapping, holographic steering, and photonic pressure), and surface acoustic wave (SAW) deflection.

In cell discrimination techniques, including sperm cell sexing applications, proper orientation, spacing, and location of the cells within the microfluidic system used to be essential to effective operation. For example, positioning and orientation are both essential being able to effectively detect the difference in fluorescence of X- and Y-chromosome bearing sperm cells stained with a DNA-intercalating dye, as both the positioning of cells within the beam of the detection laser and the orientation of the cells with respect to the detector significantly impact the amount of fluorescence detected. Alterations in the fluorescence in turn directly affect the ability to distinguish differences in the fluorescence signal between X-chromosome and Y-chromosome bearing cells.

Semen sexing instruments are typically cytometers used to sex semen by measuring DNA content of a stained bull semen sample. Once the desired population (e.g. male or female cells) is identified by the system, the instrument is able to obtain gender skew through the use of a "kill" laser. The kill laser strikes and ablates (i.e. destroys or inactivates) the undesired population of targeted cells on an individual basis through an abrupt energy pulse. The kill laser may act on the targeted cells through a number of mechanisms, including disrupting the membrane of the cells, damaging the DNA in the cells, or removing the flagellum (tail) of the cells, thereby causing the targeted cells to become infertile.

During system operation, cells that are physically closely spaced in the sample flow stream create single events in which two or more peaks are discernable. Due to kill laser charge time limitations, only events that are within the laser charge/fire time window can be shot. Targeting the correct peak in a multi-cell event is critical and is a limitation of the physical hardware. While the system is able to measure multiple peaks for a given cell event, the operation of the system results in the likely elimination of the cell desired to be kept.

This is because the system eliminates a cell due to the highest point of the pulse used in the system field programmable gate array to calculate the fire event start timer. The fire event start timer is a t=0 point for a fixed delay that is the travel time for the center (the "peak") of the cell to enter the kill laser striking zone. In most cases, semen are sexed for female gender skew after being identified as females based in part on their production of a higher intensity than males. Because of the system limitation of only hitting one peak, a choice must be made to either shoot the tall peak or the short peak. By eliminating the tall peak, and if the cells are "male—female," the cell wished to be kept (female) is hit and the cell wished to be eliminated (male) is allowed to pass.

Thus, there exists a need in the art for a sexed semen apparatus which provides the option to target either the lowest or highest peak of a multi-cell event depending on which gender is being skewed. Furthermore, there is a need in the art for a sexed semen apparatus which reduces or outright mitigates the essential reliance on proper orientation, spacing, and location of the cells within the microfluidic system for effective operation.

SUMMARY OF THE INVENTION

Therefore, it is a primary object, feature, or advantage of the present invention to improve on or overcome the deficiencies in the art.

It is still yet a further object, feature, or advantage of the present invention to provide a sexed semen apparatus determine gender of multiple peaks within an event (such as signal indicating the presence of one or more cells at the inspection region) by looking only at the event itself, still providing accurate gender skew in populations having a large percentage of multi-cell events.

It is still yet a further object, feature, or advantage of the present invention to provide a sexed semen apparatus capable of detecting dead cells in a multi-cell event.

It is still yet a further object, feature, or advantage of the present invention to provide a sexed semen apparatus capable of discriminating and sorting any remaining living cells in a multi-cell event having at least one dead cell.

It is still yet a further object, feature, or advantage of the present invention to provide a sexed semen apparatus and corresponding method of use which may be adapted to suit a wide variety of applications.

It is still yet a further object, feature, or advantage of the present invention to provide a sexed semen apparatus which sorts faster.

It is still yet a further object, feature, or advantage of the present invention to provide a sexed semen apparatus which produces a sexed semen product with a higher skew.

It is still yet a further object, feature, or advantage of the present invention to provide a sexed semen apparatus which fires the kill laser faster and reduces laser charge time.

It is still yet a further object, feature, or advantage of the present invention to provide a sexed semen apparatus which is safe to operate.

It is still yet a further object, feature, or advantage of the present invention to provide a sexed semen apparatus that is cost effective.

It is still yet a further object, feature, or advantage of the present invention to provide a sexed semen apparatus that is reliable and durable.

It is still yet a further object, feature, or advantage of the invention to provide a sexed semen apparatus that can be easily manufactured, assembled, disassembled, repaired, transported, stored, and cleaned.

It is still yet a further object, feature, or advantage of the invention to provide a sexed semen apparatus that is aesthetically pleasing.

It is still yet a further object, feature, or advantage of the present invention to incorporate the sexed semen apparatus into a system accomplishing some or all of the previously stated objectives.

It is still yet a further object, feature, or advantage of the present invention to provide methods of using, manufacturing, installing, and repairing a sexed semen apparatus accomplishing some or all of the previously stated objectives.

The previous list of objects, features, or advantages of the present invention are not exhaustive and do not limit the overall disclosure. Likewise, the following list of aspects or embodiments do not limit the overall disclosure. It is contemplated that any of the objects, features, advantages, aspects, or embodiments disclosed herein can be integrated with one another, either in full or in part, as would be understood from reading the disclosure.

According to some aspects of the present disclosure, a method to sort an undesired cell in a multi-cell fluorescent event comprises detecting a fluorescence of at least two cells physically spaced close enough such that the at least two cells create one fluorescent event, classifying each cell as an undesired cell or a desired cell based on the detection of the fluorescence of the at least two cells, allowing each desired cell to pass, and acting upon each undesired cell. In some aspects, acting on undesired cells my be accomplished using fluid switching, mechanical sorting, piezoelectric actuation, dielectrophoresis of droplets, electrolysis or electroporation, optical manipulation (e.g. optical trapping, holographic steering, and photonic pressure), and surface acoustic wave (SAW) deflection, or laser ablation.

According to some additional aspects of the present disclosure, the method further comprises introducing cell dye into the at least two cells.

According to some additional aspects of the present disclosure, the method further comprises exciting the at least two cells with a detection laser or a light emitting diode to cause the fluorescence.

According to some additional aspects of the present disclosure, the method further comprises collecting each desired cell.

According to some additional aspects of the present disclosure, the method further comprises firing a kill beam with the kill laser to ablate each undesired cell.

According to some additional aspects of the present disclosure, the method further comprises collecting each desired cell and each ablated undesired cell.

According to some additional aspects of the present disclosure, the method further comprises creating a sample flow by allowing a sheath fluid to enter a semen sexing instrument.

According to some additional aspects of the present disclosure, the fluorescence of the cell determines the sex of the at least two cells.

According to some additional aspects of the present disclosure, the method further comprises measuring a purity percentage associated with a population of cells.

According to some other aspects of the present disclosure, a method of choosing which undesired cell to destroy in a multi-cell fluorescent event comprises detecting a fluorescence of at least two cells physically spaced close enough such that the at least two cells create one fluorescent event, converting photons detected in the fluorescence of the at least two cells into an analog voltage output signal, identifying a first peak in the analog voltage output signal and associating the first peak with a first cell, identifying a second peak in the analog voltage output signal and associating the second peak with a second cell, measuring an amplitude of the first peak and an amplitude of the second peak, and defaulting a kill laser to fire a kill beam at any cells having an amplitude less than an amplitude of another cell.

According to some additional aspects of the present disclosure, the method further comprises defining a dead cell threshold percentage or an adjustable fixed value, determining the difference between the amplitude of the first peak and the amplitude of the second peak, determining if the difference between the amplitude of the first peak and the amplitude of the second peak is greater than the dead cell threshold percentage or the adjustable fixed value, and configuring the kill laser to override the defaulting step and to fire at any cells having an amplitude higher than an amplitude of another cell if the difference is greater than the dead cell threshold percentage or the adjustable fixed value.

According to some additional aspects of the present disclosure, the method further comprises filtering and digitizing the analog voltage output signal.

According to some other aspects of the present disclosure, a sexed semen product is formed as the result of executing any of the methods according to any of the aspects described above.

According to some other aspects of the present disclosure, a method of monitoring for a multi-cell fluorescent event comprises detecting fluorescence of a cell, converting photons detected in the fluorescence of the cell into an analog voltage output signal, sending the analog voltage output signal to a field programmable gate array with an analog to digital converter (ADC) state tracker machine, and monitoring a raw ADC value of the analog voltage output signal with the ADC state tracker machine.

According to some additional aspects of the present disclosure, the method further comprises defining a background threshold value, and when the raw ADC value received is less than or equal to the background threshold value, maintaining the ADC tracker state machine in an IDLE state.

According to some additional aspects of the present disclosure, the method further comprises, when the raw ADC value rises above the background threshold value, advancing the ADC tracker state machine from the IDLE state to a RISING state.

According to some additional aspects of the present disclosure, the method further comprises maintaining the ADC tracker state machine in the RISING state until the raw ADC value falls below the background threshold value, thereby returning the ADC tracker state machine to the IDLE state, or the raw ADC value falls below an immediately preceding raw ADC value but not below the background threshold value, thereby advancing the ADC tracker state machine to the PEAK state.

According to some additional aspects of the present disclosure, the method further comprises recording the immediately preceding raw ADC value as a peak value while in the PEAK state and maintaining the ADC tracker state machine in the PEAK state until the raw ADC value continues to fall below the immediately preceding raw ADC value, thereby advancing the ADC tracker state machine to the FALLING state, or the raw ADC value rises above the peak value, thereby returning the ADC tracker state machine to the RISING state.

According to some additional aspects of the present disclosure, the method further comprises maintaining the ADC tracker state machine in the FALLING state until the raw ADC value falls below the background threshold value, thereby returning to the ADC tracker state machine to the IDLE state, or the raw ADC value rises above than the immediately preceding raw ADC value, thereby advancing the ADC tracker state machine to the VALLEY state.

According to some additional aspects of the present disclosure, the method further comprises recording the immediately preceding raw ADC value as a valley value while in the VALLEY state and maintaining the ADC tracker state machine in the VALLEY state until the raw ADC value falls below the background threshold value, thereby returning to the ADC tracker state machine to the IDLE state, the raw ADC value rises above the immediately preceding value, thereby advancing the ADC tracker state machine to the RISING state and confirming occurrence of a multi-cell fluorescent event, or the raw ADC value falls below the valley value, thereby returning the ADC tracker state machine to the FALLING state.

According to some additional aspects of the present disclosure, the method further comprises generating an event with a general purpose processor or a digital signal processor to determine if the cell should be destroyed when the ADC tracker state machine transitions from the FALLING state or the VALLEY state to the IDLE state.

According to some other aspects of the present disclosure, a sexed semen system comprises a detection laser capable of exciting a sperm cell, a fluorescence detector, a computer processing unit for determining the sex of the sperm cell based on an output of the fluorescence detector, an analog to digital converter (ADC) which converts an analog voltage output signal from the fluorescence detector into a digital output signal, a field programmable gate array (FPGA) receiving the digital output, the FPGA having an ADC state tracker machine which monitors a raw ADC value of the analog voltage output signal to determine if a multi-cell fluorescent event has occurred, and if so, to classify each sperm cell as desirable or undesirable, and a kill laser for destroying an undesirable sperm cell.

According to some additional aspects of the present disclosure, the system further comprises a sheath fluid encapsulating the sperm cell.

According to some additional aspects of the present disclosure, the system utilizes inertial flow focusing.

According to some additional aspects of the present disclosure, the system further comprises a first detection laser lens assembly.

According to some additional aspects of the present disclosure, the system further comprises a second detection laser lens assembly.

According to some additional aspects of the present disclosure, the system further comprises a kill laser lens assembly.

According to some additional aspects of the present disclosure, the fluorescence detector is an avalanche photodiode (APD) sensor.

According to some additional aspects of the present disclosure, the ADC tracker state machine includes an IDLE state, a RISING state, a PEAK state, a FALLING state, and a VALLEY state.

According to some additional aspects of the present disclosure, the system further comprises a general purpose processor (GPP) or a digital signal processor (DSP) using a defined gate to generate a fire signal to the FPGA with the option of the FPGA to make a kill decision based on the defined gate.

According to some additional aspects of the present disclosure, the system further comprises a low pass filter for passing signals with a frequency lower than a selected cutoff frequency.

These or other objects, features, and advantages of the present invention will be apparent to those skilled in the art after reviewing the following detailed description of the illustrated embodiments, accompanied by the attached drawings.

Various embodiments of the present disclosure illustrate several ways in which the present invention may be practiced. These embodiments will be described in detail with reference to the drawings, wherein like reference numerals represent like parts throughout the several views. Reference to specific embodiments does not limit the scope of the present disclosure and the drawings represented herein are presented for exemplary purposes.

DETAILED DESCRIPTION OF THE INVENTION

Definitions—Introduction

The following definitions and introductory matters are provided to facilitate an understanding of the present invention. Unless defined otherwise, all technical and scientific terms used herein have the same meaning as commonly understood by one of ordinary skill in the art to which embodiments of the present invention pertain.

In communications and computing, a computer readable medium is a medium capable of storing data in a format readable by a mechanical device. The term "non-transitory" is used herein to refer to computer readable media (CRM) that store data for short periods or in the presence of power such as a memory device or random access memory (RAM).

One or more embodiments described herein can be implemented using programmatic modules, engines, or components. A programmatic module, engine, or component can include a program, a sub-routine, a portion of a program, or a software component or a hardware component capable of performing one or more stated tasks or functions. As used herein, a module or component can exist on a hardware component independently of other modules or components. Alternatively, a module or component can be a shared element or process of other modules, programs or machines.

The terms "a," "an," and "the" include plural referents unless context clearly indicates otherwise. Similarly, the word "or" is intended to include "and" unless context clearly indicate otherwise. The word "or" means any one member of a particular list and also includes any combination of members of that list.

The terms "invention" or "present invention" as used herein are not intended to refer to any single embodiment of the particular invention but encompass all possible embodiments as described in the specification and the claims.

The term "about" as used herein refers to variation in the numerical quantities that can occur, for example, through typical measuring techniques and equipment, with respect to any quantifiable variable, including, but not limited to, mass, volume, time, distance, angle, wave length, frequency, voltage, current, and electromagnetic field. Further, given solid and liquid handling procedures used in the real world, there is certain inadvertent error and variation that is likely through differences in the manufacture, source, or purity of the ingredients used to make the compositions or carry out the methods and the like. The claims include equivalents to the quantities whether or not modified by the term "about."

The term "configured" describes an apparatus, system, or other structure that is constructed to perform or capable of performing a particular task or to adopt a particular configuration. The term "configured" can be used interchangeably with other similar phrases such as constructed, arranged, adapted, manufactured, and the like.

Terms such as first, second, vertical, horizontal, top, bottom, upper, lower, front, rear, end, sides, concave, convex, and the like, are referenced according to the views presented. These terms are used only for purposes of description and are not limiting unless these terms are expressly included in the claims. Orientation of an object or a combination of objects may change without departing from the scope of the invention.

The apparatuses, systems, and methods of the present invention may comprise, consist essentially of, or consist of the components of the present invention described herein. The term "consisting essentially of" means that the apparatuses, systems, and methods may include additional components or steps, but only if the additional components or steps do not materially alter the basic and novel characteristics of the claimed apparatuses, systems, and methods.

The following embodiments are described in sufficient detail to enable those skilled in the art to practice the invention however other embodiments may be utilized. Mechanical, procedural, and other changes may be made without departing from the spirit and scope of the invention. Accordingly, the scope of the invention is defined only by the appended claims, along with the full scope of equivalents to which such claims are entitled.

Overview

Figure 1:
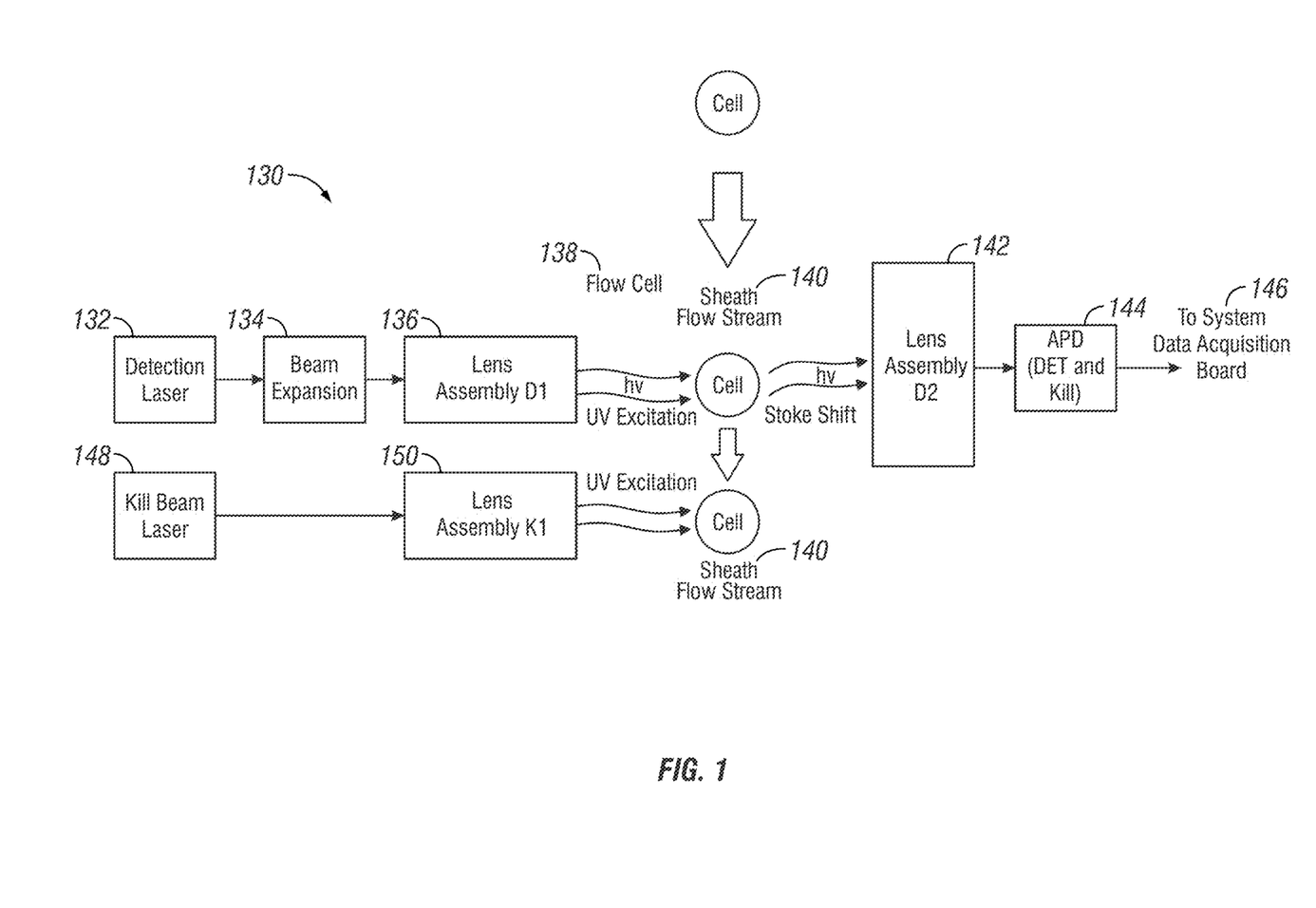
FIG. 1 shows a diagram of the sexed semen system implementation wherein a single detector is used for detection and kill in the instrument according to some aspects of the present disclosure.

According to a non-limiting example of the present disclosure, FIG. 1 shows a diagram of an exemplary system implementation which includes components of an optimized semen sexing instrument or cytometer 130. According to this non-limiting example, the optimized semen sexing instrument or cytometer 130 has a detection laser or light emitting diode 132 used to excite the cell dye for DNA measurement. In other systems according to the present invention, DNA content or other sperm cell characteristics can be detected using other means know to persons skilled in the art. The detection laser 132 can benefit by utilizing beam conditioning 134 and a first detection laser lens assembly 136 to achieve the correct spot size of a detection spot at the flow cell 138.

The system of the present invention will generally utilize a microfluidic fluid focusing subsystem, which may use one or more hydrodynamic, geometric, or inertial focusing elements to position, orient, and/or space the cells. The microfluidic subsystem may also include a nozzle in combination with other elements. A sample fluid containing cells enters a microfluidic channel in the microfluidic subsystem of the optimized semen sexing instrument or cytometer 130 and moves cells through the system flow cell 138. As the sample flow stream 140 moves the cells, the beam conditioning 134 and a first detection laser lens assembly 136 elements steer a detection pulse emitted by the detection laser 132 into the sample flow stream 140. The detection pulse illuminates a cell within the sample flow, and the fluorescent dye bound the DNA of the cell produces a fluorescent emission event, which is directed onto a surface of a detector 144 by a second detection laser lens assembly 142.

The detector 144 is typically an avalanche photodiode (APD) sensor and the optics for measuring the fluorescence signal from the cell during interrogation. The detector may also be a photomultiplier tube (PMT), photodiode array (PDA), or similar photosensitive detector. The detector 144 is the sensor used to classify male and female populations of cells and aids in determining which cells are undesirable. The measurement taken by the detector 144 is used in a custom board stack to convert photons to an analog voltage output signal 152 which is then sent to the data acquisition (DAQ) board 146.

All cells then travel inside the flow cell 138 from the detection spot to a kill spot. A kill laser 148 of the improved semen sexing instrument or cytometer 130 is used to destroy undesirable cells. In other systems according to the present invention, the kill laser may be replaced with a different sorting element, such as a fluid switch or piezoelectric actuator, a mechanical switch or other mechanical sorting device, dielectrophoretic apparatus, electrodes (for e.g. electrolysis, electroporation, or cavitation), optical elements (e.g. lasers and associated optics, fiber optics, and waveguides) for photonic manipulation (e.g. optical trapping, holographic steering, and photonic pressure), and surface acoustic wave (SAW) devices. The kill laser 148 has a "high" energy at a short recharge time, a stable pulse to pulse consistency, and a pulse on demand operation.

A kill laser lens assembly 150 can direct the kill beam to the kill spot in the flow cell 138 and establish the spot size. The shape of the kill beam is typically a knife blade shape. Additionally, the energy density of the kill beam, tight focusing of the cell stream, and alignment of the kill laser, are all critical factors to consider for proper operation of the sexed semen system.

Most often during system operation, the detection pulse illuminates a single cell within the sample flow, as is depicted in FIG. 1. However, there are occasionally cells that so physically closely spaced in the sample flow stream 140 that the detection pulse illuminates more than one cell, resulting in a multi-cell event, as is depicted in FIG. 2.

Figure 2:
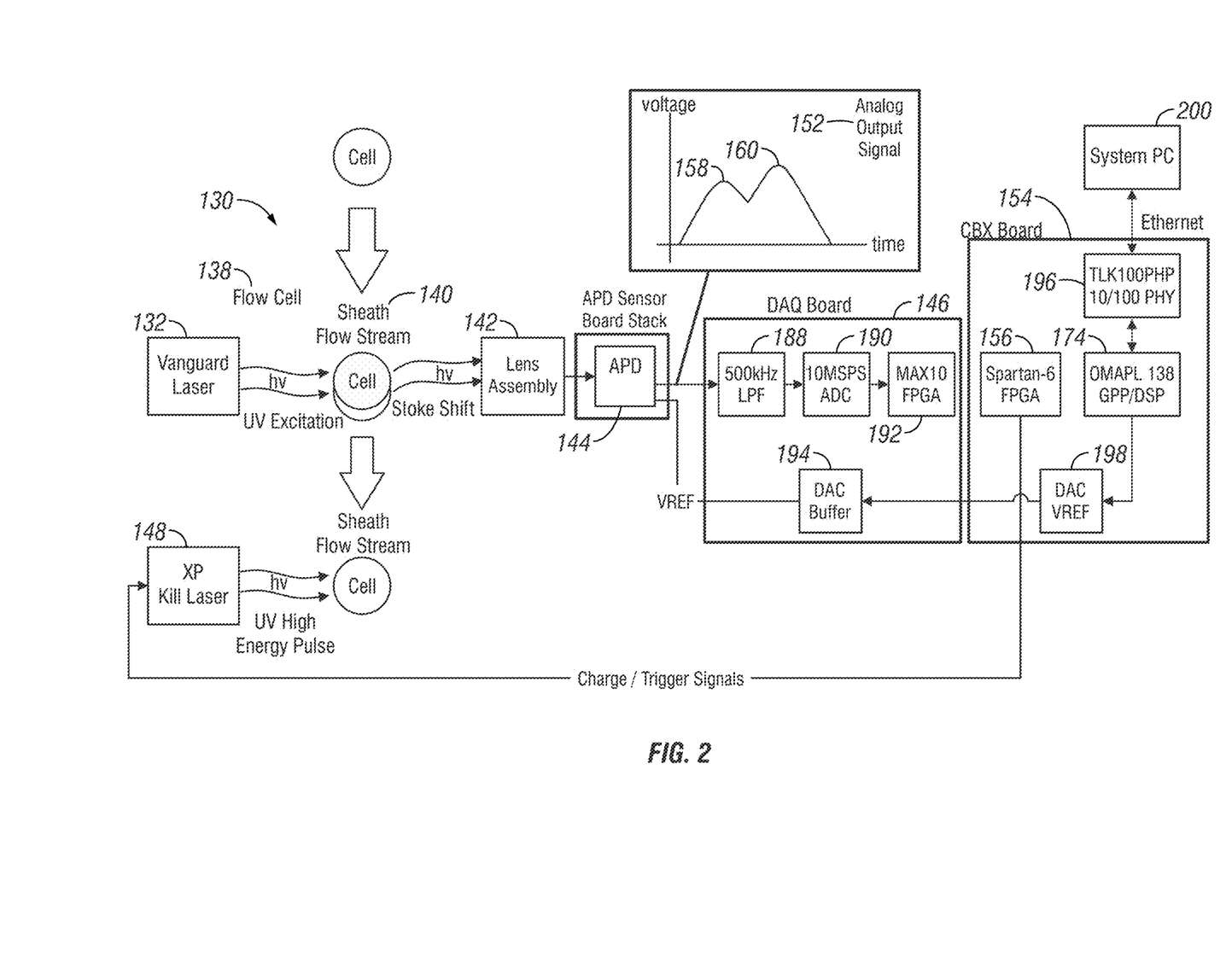
FIG. 2 shows a diagram of a sexed semen system implementation which provides the option to target either the lowest or highest peak within a multi-cell event depending on which gender is being skewed, according to some aspects of the present disclosure.

Referring now to FIG. 2, the DAQ board 146 filters and digitizes the analog voltage output signal 152 from the APD board stack. The DAQ board 146 sends the digitized signal to the control box (CBX) interface board 154, and more particularly to a FPGA 156 of the CBX interface board 154.

In a multi-cell event, the analog voltage output signal 152 typically has a first peak 158 and a second peak 160. The first peak 158 and the second peak 160 are discernable from one another. The first peak 158 and the second peak 160 will have different amplitudes if the cells associated with each of the peaks are of different sexes. For example, if the cells traveling through the sample flow stream 140 are "female-male," the first peak 158 will be the "tall peak" and the second peak 160 will be the "short peak." If the cells traveling through the sample flow stream 140 are "male-female," the first peak 158 will be the "short peak" and the second peak 160 will be the "tall peak." As will be discussed later on, there are other reasons which cause the amplitude of each of the peaks to vary. A "male-female" multi-cell event is depicted in FIG. 2, whereas a "female-male" multi-cell event is depicted in FIG. 3.

Figure 3:
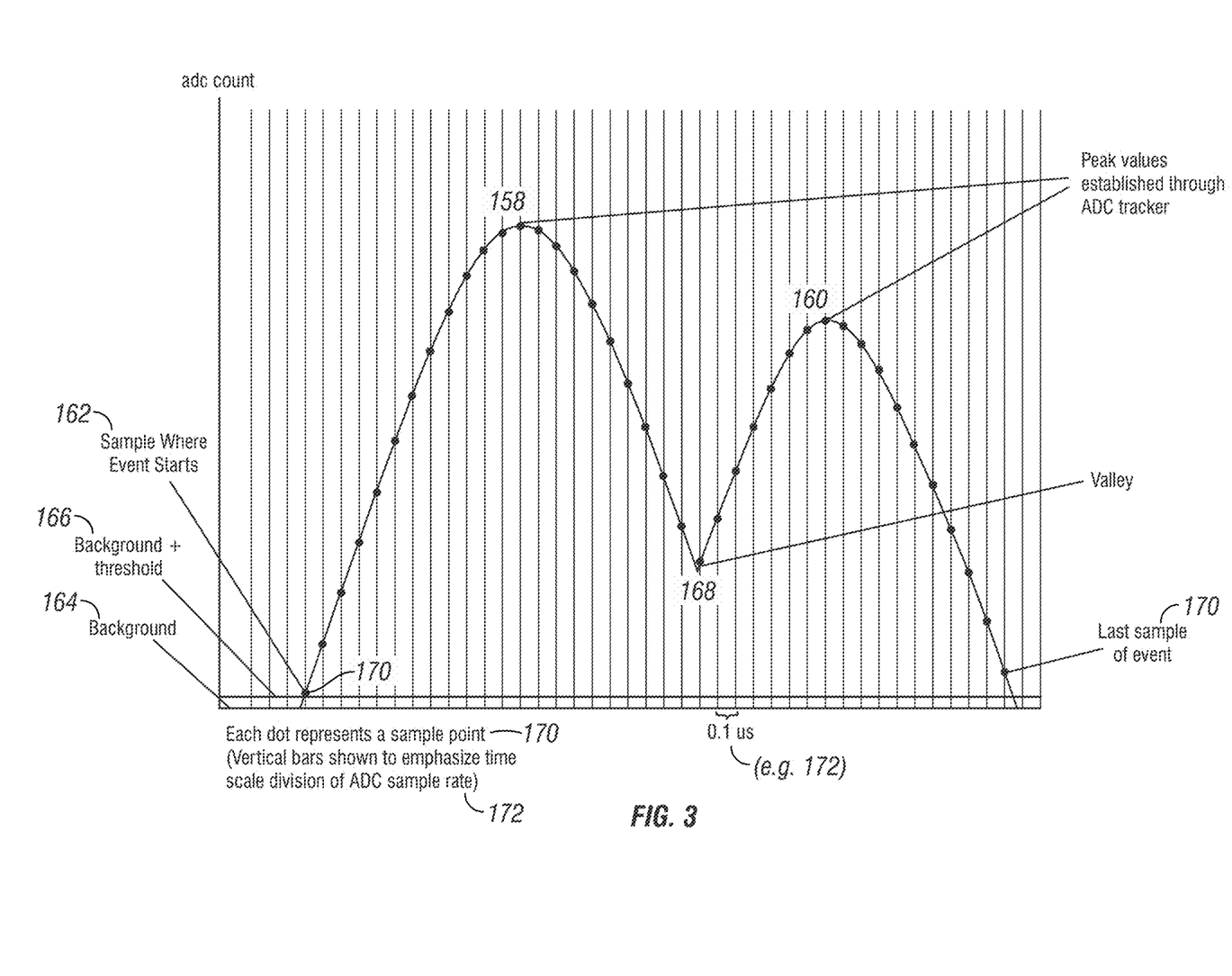
FIG. 3 illustrates multi-peak pulse digitalization. More particularly, a multi-cell event is shown wherein two discernable peaks are present and are measured as a function of time with respect to analog voltage system output, according to some aspects of the present disclosure.

Several critical points are indicated in the analog voltage output signal 152 of FIG. 3, such as the start of the event 162, the background 164, the background threshold value 166, the valley 168, and peak values occurring at the first peak 158 and the second peak 160. The background 164 is the digitized signal stream of the raw ADC value that is below the background threshold value 166. The start of the event 162 occurs when the value of a sample point 170 exceeds the background threshold value 164 and signals to the FPGA 156 that an event is starting.

Sample points 170 will continue to be gathered at the ADC sample rate 172 until the event ends and the last sample point 170 of the event is collected. The vertical bars in FIG. 3 are shown to emphasize the time scale division of the ADC sample rate 172. For example, in a preferred embodiment, the ADC sample rate 172 comprises one sample point 170 per every 0.1 µs. The unique sample point 170 which occurs at the inflection point where the second peak 160 begins in a multi-peak event defines the valley 168 and is known as the valley value.

The FPGA 156 analyzes the incoming ADC sample data (i.e., the analog voltage output signal 152) and performs all cell event flags and pulse peak/area calculations. The FPGA 156 analyzes a multi-cell event based solely on the event's properties and will decide which cell to eliminate in accordance with the cell process shown in FIG. 4. For non-multipeak events, a general purpose processor (GPP)/digital signal processor (DSP) 174 uses a defined gate and generates the fire signal to the FPGA 156 (the majority of the events in the optimized semen sexing instrument or cytometer 130) with the option of the FPGA to make a kill decision based on the defined gate.

Figure 4:
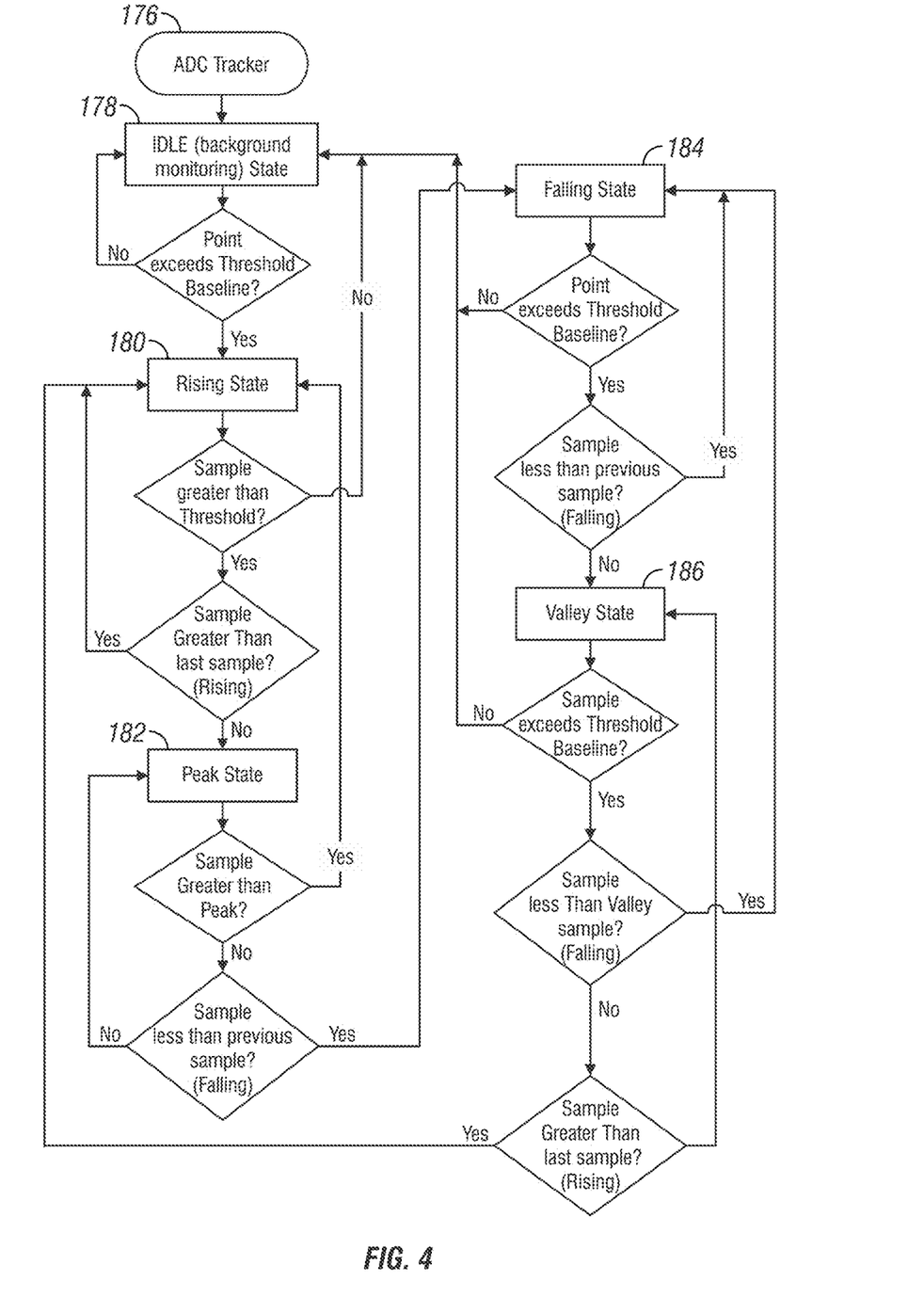
FIG. 4 shows an illustrative high-level diagram of a cell process employed by an analog to digital converter (ADC) tracker state machine within a field programmable gate array (FPGA), according to some aspects of the present disclosure.

Referring now to FIG. 4, the ADC tracker state machine 176 is how the Spartan 6 FPGA is able to determine whether the multi-peak event has taken place and/or monitor for multi-peak events which have yet to occur. The ADC tracker state machine 176 provides information for making targeting decisions. In almost all cases, when a raw ADC value is received that is less than or equal to the background threshold value 166, the ADC tracker state machine 176 will go to the background (IDLE) state 178. The background threshold value 166 is used to reduce the number of events reported due to very small bumps in the ADC data (background noise, e.g., background 164). A higher background threshold value 166 yields fewer false events, while reducing the accuracy of the area calculation. The ADC tracker state machine 176 stays in the IDLE state 178 until a raw ADC value greater than the background threshold value 166 is received. When a raw ADC value greater than the background threshold value 166 is received, the ADC tracker state machine 176 advances to the RISING state 180.

The ADC tracker state machine 176 stays in the RISING state 180 until: (1) the received raw ADC value goes back below the background threshold value 166 and the ADC tracker state machine 176 returns to the IDLE state 178 without producing an event; or (2) the received raw ADC value is less than the previous received raw ADC value, advancing the ADC tracker state machine 176 to the PEAK state 182.

The ADC tracker state machine 176 stays in the PEAK state 182 if the received raw ADC value is greater than the previous value, but not greater than the saved peak value (in this case it is hard to determine if the ADC values are rising or falling). The ADC tracker state machine 176 leaves the PEAK state 182 when: (1) the received raw ADC value is less than the previous value, advancing the ADC tracker state machine 176 to the FALLING state 184; or (2) the received raw ADC value is greater than the saved peak value, returning the ADC tracker state machine 176 to the RISING state 180, which could occur if there was a brief (single sample) drop while the ADC data was otherwise rising.

The ADC tracker state machine stays in the FALLING state 184 if the received raw ADC data is less than the previous value and still greater than the background threshold value 166. The ADC tracker state machine 176 leaves the FALLING state 184 when: (1) the received raw ADC value is less than or equal to the background threshold value 166, returning to the ADC tracker state machine 176 to the IDLE state 178, thereby generating an event interrupt to the GPP/DSP 174; or (2) the received raw ADC value is greater than the previous value, advancing the ADC tracker state machine 176 to the VALLEY state 186.

The ADC tracker state machine 176 stays in the VALLEY state 186 if the received raw ADC value is greater than the background threshold value 166, but less than the previous value and greater than or equal to the saved valley value 168 (in this case it is hard to determine if the ADC values are rising or falling). The ADC tracker state machine 176 leaves the VALLEY state 186 when: (1) the received raw ADC value is less than or equal to the background threshold value 166, returning to the ADC tracker state machine 176 to the IDLE state 178, thereby generating an event interrupt to the GPP/DSP 174; (2) the received raw ADC value is greater than the previous value, advancing the ADC tracker state machine 176 to the RISING state 180, which indicates a multi-cell (multi-peak) event; or (3) the received raw ADC value is less than the saved valley value, returning the ADC tracker state machine 176 to the FALLING state 184, which could occur if there was a brief (single sample) bump while the ADC data was otherwise falling.

Once the event is completed, which is achieved by a return to IDLE state 178, the peak locations 158, 160 in time can be retrieved and used for making comparisons of the peak amplitudes and timing information for the peak location. A kill decision is derived purely internally by the FPGA 156 using the conditions described in Solution 1 and Solution 2 therefore eliminating the need to wait for a GPP or DSP predefined gate on multi-peak events. Thus, the fire queue can be filled by a multi-peak event without knowledge of the gate, thereby allowing a near-instantaneous classification and immediate application of the kill strategy.

Preferred Embodiment and Components

In a preferred embodiment, the detection laser 132 is a Vanguard 355/350 laser, which has become the current industry standard for semen evaluation.

The Vanguard 355/350 laser may be "over" powered for a single station of detection.

In a preferred embodiment, the DAQ board 146 includes a low pass filter (LPF) 188, an ADC 190, a FPGA 192, and a digital to analog converter (DAC) buffer 194. The LPF 188 passes signals with a frequency lower than a selected cutoff frequency (e.g., 500 kHz, as is noted in FIG. 2) and attenuates signals with frequencies higher than the cutoff frequency. The ADC 190 is an electronic integrated circuit used to convert the analog voltage output signal 152 to digital or binary form. The ADC 190 can have a sample rate of 10 megasamples per second (MSPS). The DAC buffer 194 is used to drive an analog reference signal for controlling the voltage bias and therefore the opto-electronic gain of the APD 144.

In a preferred embodiment, the kill laser 148 and the detection pulse have the same wavelength. Operation of kill and detection at the same wavelength allows for the use of a single cell stain (dye) because the stained DNA within the cell will fluoresce a second time. In other words, the cell undergoes two separate fluorescent events: a first event when illuminated by the detection laser; and a second event when struck by the kill beam. The kill laser 148 can be a 355 nanometer Q-switch laser which leverages the dye in the cells and disrupts the membrane of the cells. Oversaturation/emission of the dye renders the cells infertile because ultraviolet (UV) light (e.g. 355 nanometers) is known to cause DNA damage. The present disclosure appreciates however that different wavelengths of a kill laser (e.g. infrared) would also kill sperm cells, but with a different mechanism.

In a preferred embodiment, the CBX interface board 154 includes the FPGA 156, the GPP/DSP 174, physical layer (PHY) 196, and a DAC voltage reference (VREF) 198. In one embodiment, the FPGA 156 can be a Spartan 6 FPGA. The GPP/DSP 174 is located on the control box (CBX) interface board. In one embodiment, the GPP/DSP is an OMAP-L138. The PHY 196 connects a link layer device (often called MAC as an acronym for medium access control) to a physical medium such as an optical fiber or copper cable. The DAC VREF 198 provides an accurate and stable point for digital to analog conversions.

Figure 5:
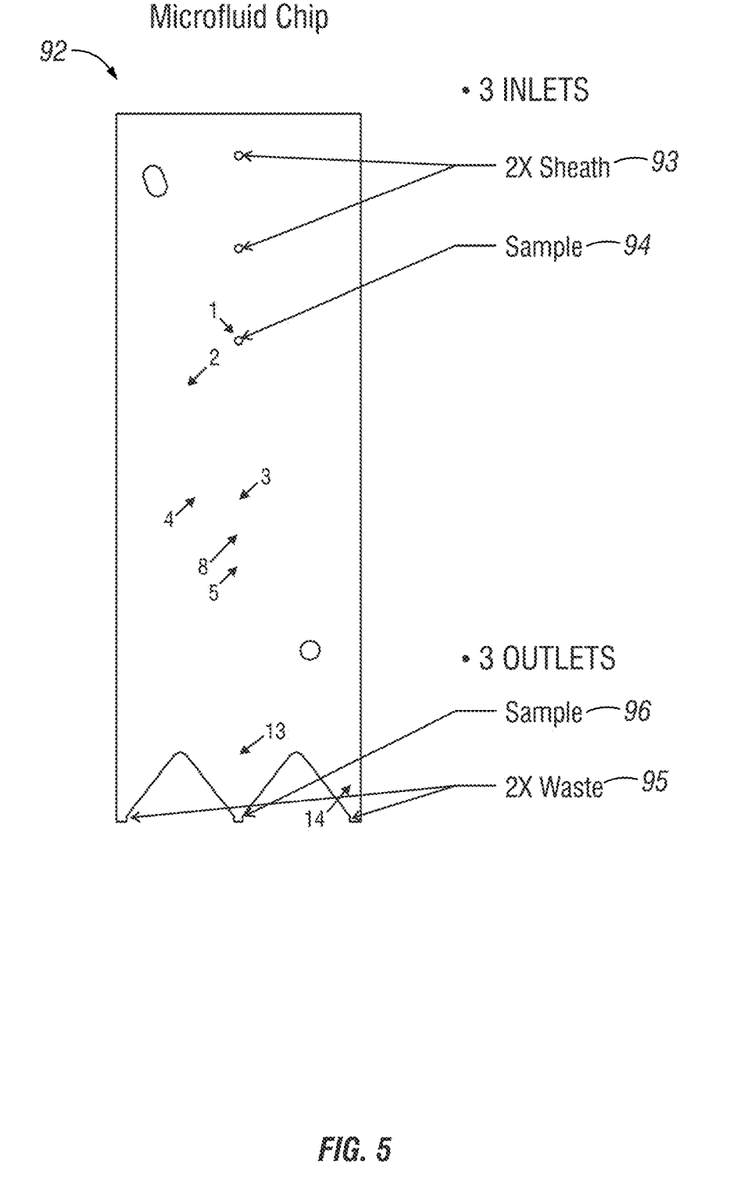
FIG. 5 shows a microfluidic chip according to some aspects of the present disclosure.

In one embodiment the microfluidics subsystem comprises a mass flow controller which includes a microfluidic chip 92 having two sheath inlets 93, a sample inlet 94, two waste outlets 95, and a sample outlet; sheath outlets; a sheath tube; a sheath supply; and controller bleed ports. The mass flow controller utilizes differential pressure-based flow metering, and the controller bleed ports are capable of cleaning, flushing, or removing air from the sexed semen system.

Solution 1—Female Gender Skew

In Table 1 (below), the lowest peak is always shot, and a method is provided to adjust laser charge time to hit events spaced as closely as possible. A cell which has been formatted in bold indicates that the cell has been shot.

| Peak 158 | Peak 160 | Comments |
|---|---|---|
| M | M | Either the first peak 158 or the second peak 160 could be targeted; this makes no difference from a purity standpoint. |
| F | F | |
| M | F | |
| F | M | |
| D | M | Dead cells only make up about 10% of the cell population during a fresh bull run, therefore these events are not weighted as heavily as the four M/F events listed above. These events are "dead weight" events. |
| D | F | |
| D | D | |
| M | D | |
| F | D | |

Because the dead population is a smaller percentage of the overall cell population (typically around 10%), it is assumed the dead values listed have a lower weight to the overall purity result. This has less of an impact on skew due to its lower overall percentage as "dead weighted average" or simply, "dead weight." The first four events listed are known as "live multiple-cell events" and occur much more frequently.

For this implementation, three females pass and one male passes for nominal live multiple-cell events (75% skew) and two females pass and two males pass for dead weight multiple-cell events (50% skew).

Solution 2—Female Gender Skew

The detection system may be further optimized such that the possibility of shooting dead cells is eliminated. This will be a simple threshold implementation where cell peak-heights below a fixed value will be determined to be "dead" and not fired upon to save laser lifetime and also improve laser recharge time. These dead events will simply be excluded from the laser firing queue. The dead events are still reported to the system graphical user interface (GUI). The dead cell threshold value can be a user set value or hard coded. The dead cell threshold value may be calculated from the initial histogram at machine setup. The dead cell threshold value may be fixed for the duration of the run.

For this solution, if the difference in amplitude is greater than a user defined dead cell percentage (a reasonable threshold would be 25%) this indicates it is extremely likely to have a dead cell and a living cell. This condition allows the identification of "dead weight" events and optimizes a multi-peak events purity probability.

In Table 2 (below), the lowest peak is always shot, except if the difference between the two peaks 158, 160 is greater than a given threshold percentage, and a method is provided to adjust laser charge time to hit events spaced as closely as possible. A cell which has been formatted in bold indicates that the cell has been shot.

| Peak 158 | Peak 160 | Comments |
|---|---|---|
| M | M | Either the first peak 158 or the second peak 160 could be targeted; this makes no difference from a purity standpoint. |
| M | F | |
| F | M | |
| F | F | |
| D | M | The dead cell passes, thereby having no impact on skew. For a DD ("dead cell – dead cell") event, the event will be treated like a MM or FF event from an algorithmic standpoint. |
| D | F | |
| D | D | |
| M | D | |
| F | D | |

By determining that a cell is likely to be a dead cell due to a large difference in signal amplitude, three females pass and one male passes for nominal live multiple-cell events (75% skew) and the dead cells all pass, with the possible exception of the dead-dead combination in which case the laser may not fire at all.

Mathematical Modeling of Solutions 1 & 2

Table 3 (below) models the calculated probability of each possible two-cell event wherein d is the percentage of dead cells in the total population and it is assumed there are an equal number of male cell and female cells in remaining living cells.

| Peak 158 | Peak 160 | Comments |
|---|---|---|
| M | M | $0.25 - 0.5 * d - 0.25 * d^2$ |
| M | F | $0.25 - 0.5 * d - 0.25 * d^2$ |
| F | M | $0.25 - 0.5 * d - 0.25 * d^2$ |
| F | F | $0.25 - 0.5 * d - 0.25 * d^2$ |
| D | M | $0.5 * d - 0.5 * d^2$ |
| D | F | $0.5 * d - 0.5 * d^2$ |
| D | D | $d^2$ |
| M | D | $0.5 * d - 0.5 * d^2$ |
| F | D | $0.5 * d - 0.5 * d^2$ |

Thus, for Solution 1, the skew of living cells in output is:

$$(0.75 - 0.5 * d - 0.25 * d^2)/(1 - d^2).$$

Note that for Solution 1, a maximum skew of 75% can only be achieved when dead cells are not present. As the dead cell population increases, the skew declines rapidly. For example, the skew is estimated to be 70.5% when only 10% of a population of cells are dead. The skew will drop to approximately 66.7% when the percentage of dead cells increases to 20%.

For Solution 2, the skew of living cells in multi-cell events is 75%, irrespective of the percentage of dead cells.

Actual implementation of Solutions 1 and 2 will not necessarily result in the theoretical expectation associated with the mathematical models provided herein; however, said implementation of Solutions 1 and 2 will still result in a significantly purer product (typically by several percentage points) for a given throughput.

User Operability and Computer Connectivity

There is typically a non-transitory computer readable medium 200 running the system software capturing processed data. The non-transitory computer readable medium 200 is used to operate the optimized semen sexing instrument or cytometer 130 and is where a user defined gate is generated. The user defined gate is based on an input received from a user through a user interface ("UI"). The input from the user interface ("UI") can be sent to a microcontroller to control operational aspects of the sexed semen system and could include a combination of digital and analog input and/or output devices or any other type of UI input/output device required to achieve a desired level of control and monitoring for a device. A user interface is how the user interacts with the optimized semen sexing instrument or cytometer 130. The user interface could be a digital interface, a command-line interface, a graphical user interface ("GUI"), or any other way a user can interact with a machine. For example, the user interface module can include a display and input devices such as a touchscreen, knobs, dials, switches, buttons, etc. More specifically, the display could be a liquid crystal display ("LCD"), a light-emitting diode ("LED") display, an organic LED ("OLED") display, an electroluminescent display ("ELD"), a surface-conduction electron emitter display ("SED"), a field-emission display ("FED"), a thin-film transistor ("TFT") LCD, a bistable cholesteric reflective display (i.e., e-paper), etc. The user interface also can be configured with a microcontroller to display conditions or data associated with the main device in real-time or substantially real-time.

The non-transitory computer readable medium 200 typically includes an Ethernet port. However, the present disclosure is not intended to be limited to the use of the non-transitory computer readable medium 200 with an Ethernet port.

The sexed semen system may include additional electrical components such as an intelligent control and communication components with the non-transitory computer readable medium 200. Examples of such intelligent control units may be tablets, telephones, handheld devices, laptops, user displays, or generally any other computing device capable of allowing input, providing options, and showing output of electronic functions. Still further examples include a microprocessor, a microcontroller, or another suitable programmable device, and a memory. The sexed semen system can also include other components and can be implemented partially or entirely on a semiconductor (e.g., a field programmable gate array (FPGA)) chip, such as a chip developed through a register transfer level (RTL) design process.

The memory includes, in some embodiments, a program storage area and a data storage area. The program storage area and the data storage area can include combinations of different types of memory, such as read-only memory (ROM), random access memory (RAM) (e.g., dynamic RAM (DRAM), synchronous DRAM (SDRAM), etc.), electrically erasable programmable read-only memory (EEPROM), flash memory, a hard disk, an SD card, or other suitable magnetic, optical, physical, or electronic memory devices.

Generally, the non-transitory computer readable medium 200 operates under control of an operating system stored in the memory. The non-transitory computer readable medium 200 implements a compiler which allows a software application written in a programming language such as COBOL, C++, FORTRAN, or any other known programming language to be translated into code readable by the central processing unit. After completion, the software application accesses and manipulates data stored in the memory of the non-transitory computer readable medium 200 using the relationships and logic that was generated using the compiler.

In one embodiment, a software application with instructions implementing the operating system and the compiler are tangibly embodied in the computer-readable medium 200. When the instructions are read and executed by the non-transitory computer readable medium 200, the non-transitory computer readable medium 200 performs the steps necessary to implement and/or use the present invention. A software application and/or operating instructions may also be tangibly embodied in the memory and/or data communications devices, thereby making the software application a product or article of manufacture according to the present invention.

A communications module can be included with the sexed semen system and can be configured to connect to and communicate with a controller, such as a computer, tablet, server, or other computing device. This could allow the sexed semen system to provide data or other information (e.g., warnings, status, notices, etc.) associated with the sexed semen system to a remote location of the controller to allow the real-time information and stored information for the sexed semen system. The information could be used to determine issues, forecast, or otherwise track information related to the sexed semen system. The communication could also be in the form of inputs such that the communication could include a command to the sexed semen system from a remote location.

In some embodiments, the sexed semen system includes a first communications module for communicating with a secondary device (another sexed semen system or remote controller), and/or a second communications module for communicating with a central location (server, computer, or other master controller). For sake of simplicity, the term "communications module" herein applies to one or more communications modules individually or collectively operable to communicate with both the sexed semen system and the central location.

The communications module communicates with the central location through the network. In some embodiments, the network is, by way of example only, a wide area network (WAN) (e.g., a global positioning system (GPS), a TCP/IP based network, a cellular network, such as, for example, a Global System for Mobile Communications (GSM) network, a General Packet Radio Service (GPRS) network, a Code Division Multiple Access (CDMA) network, an Evolution-Data Optimized (EV-DO) network, an Enhanced Data Rates for GSM Evolution (EDGE) network, a 3GSM network, a 4GSM network, a Digital Enhanced Cordless Telecommunications (DECT) network, a Digital AMPS (IS-136/TDMA) network, or an Integrated Digital Enhanced Network (iDEN) network, etc.), although other network types are possible and contemplated herein. In certain embodiments, the network is a GSM or other WAM which is operable to allow communication between the communications module and the central location during moments of low-quality connections, such as but not limited to when the sexed semen system is near a window.

The network can be a local area network (LAN), a neighborhood area network (NAN), a home area network (HAN), or personal area network (PAN) employing any of a variety of communications protocols, such as Wi-Fi, Bluetooth, ZigBee, near field communication (NFC), etc., although other types of networks are possible and are contemplated herein. Communications through the network by the communications module or the controller can be protected using one or more encryption techniques, such as those techniques provided in the IEEE 802.1 standard for port-based network security, pre-shared key, Extensible Authentication Protocol (EAP), Wired Equivalency Privacy (WEP), Temporal Key Integrity Protocol (TKIP), Wi-Fi Protected Access (WPA), and the like.

Finally, it is noted the present disclosure contemplates components of the sexed semen system may be powered in a number of ways. The components of the system can be hard-wired, cord and plug connected, or otherwise powered, such as to AC power plugs and sockets. A hardwired component is one where the building wiring method attaches to the component in a more permanent fashion. This will involve splicing of wires inside the component or in a junction box. Cord and plug connected components have a cord with a molded plug that is either factory or field installed on the component. The component is then ready to be plugged in to a receptacle in the location it is permanently installed. The hard-wired power source could be on a power grid, or could be a separate generator, battery, or other source. The wire could provide power over Ethernet or via USB cable, such as if the system is connected in such a manner. Still further, it is contemplated that the system be self-powered or include on-board power, in that there is no wiring to a separate power source. Such a configuration could include batteries in the system, such as non-rechargeable (e.g., dry battery) or rechargeable (e.g., Lithium-ion) type batteries. Still further, other types of power, such as, but not limited to, solar, piezoelectric sources, and the like, which can provide additional amounts of power.

Two tests were performed to determine the performance of Kill Strategy A (new kill optimization) to Kill Strategy B (previous method).

Test 1 compared the product purity and product yield between Kill Strategy A (n=35) to Kill Strategy B (n=755). All other system parameters remained constant including cell rate, laser charge time, and laser energy. Several instruments were implemented with Kill Strategy A as a comparison to a larger population of instruments implemented with Kill Strategy B. The resulting batches produced from each instrument strategy were compared for product purity. Purity is displayed as Kill Strategy A minus Kill Strategy B. Product Yield is displayed as the ratio of Kill Strategy A to Kill Strategy B.

Test 2 compared the product purity and product yield between Kill Strategy A (n=113) to Kill Strategy B (n=284). All other system parameters remained constant except for cell rate. Kill Strategy A cell rate operated at a cell rate 30% higher than Kill Strategy B.

Figure 6:
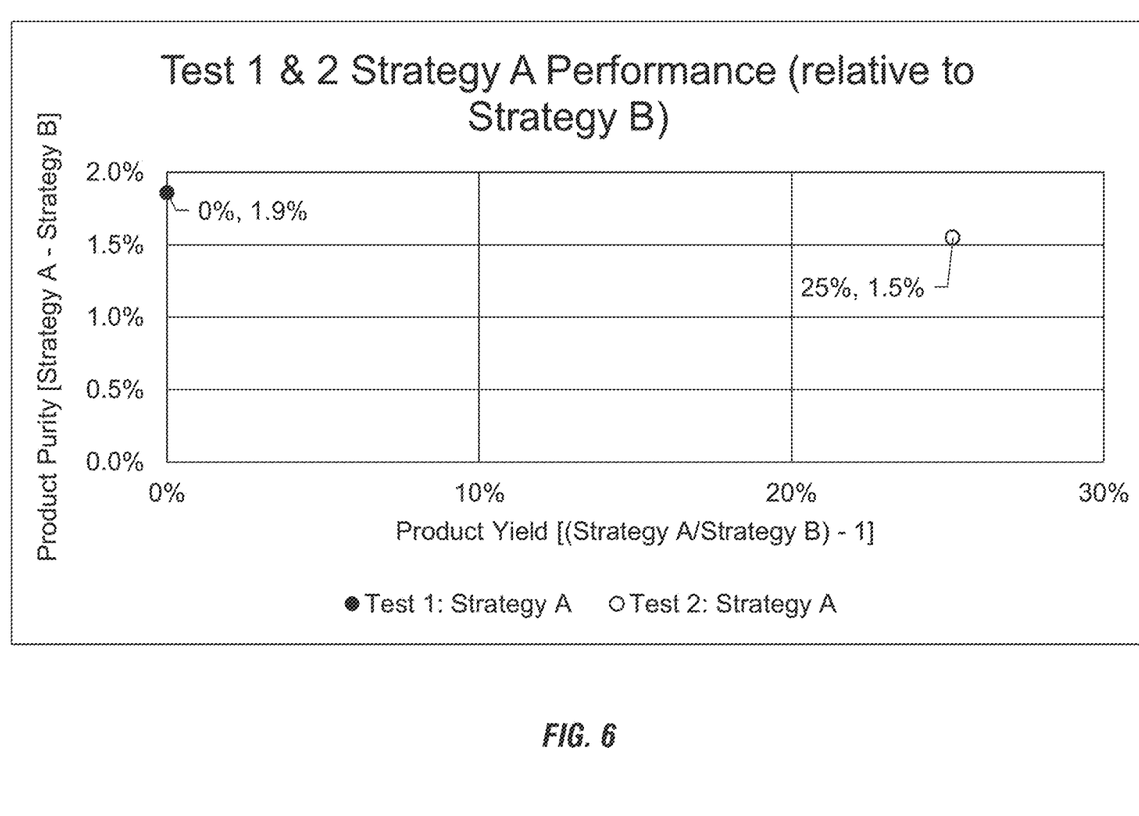
FIG. 6 illustrates the increase in purity of this novel kill optimization strategy compared to the previous approach.

Several instruments were implemented with Kill Strategy A as a comparison to a larger population of instruments implemented with Kill Strategy B. The resulting batches produced from each instrument strategy were compared for product purity. Purity is displayed as Kill Strategy A minus Kill Strategy B. Product Yield is displayed as the ratio of Kill Strategy A to Kill Strategy B. These results are presented in FIG. 6.

When implemented into a semen sexing cytometer, the multi-event kill strategy increased both purity and yield. The multi-event kill strategy as described herein was used on a laser ablation semen sexing instrument, operating a kill laser with a four sub-millisecond charge time. the improved sorting strategy increased purity by 2%, compared to previously implemented strategy at the same throughput. At a throughput increase of 30%, the purity and yield increased by 1.5% and 25%, respectively, over control operation. At a throughput increase of 40%, the purity and yield increased by 3% and 37%, respectively.

Overall, these results demonstrate that the improved sorting strategy improved operation of the semen sexing system both by increasing the efficacy sexing (as demonstrated by improved skew) and increased efficiency (as demonstrated by increased productivity) under all conditions tested. Importantly, these improvements in purity and yield at an operational level on a sexing apparatus can translate into as much as a 50% improvement in the production of sexed semen, compared to currently available commercial semen sexing process.

From the foregoing, it can be seen that the present invention accomplishes at least all of the stated objectives.

LIST OF REFERENCE NUMERALS

The following list of reference numerals is provided to facilitate an understanding and examination of the present disclosure and is not exhaustive. Provided it is possible to do so, elements identified by a numeral may be replaced or used in combination with any elements identified by a separate numeral. Additionally, numerals are not limited to the descriptors provided herein and include equivalent structures and other objects possessing the same function.
92 microfluidic chip
93 sheath inlets
94 sample inlet
95 waste outlets
130 optimized sexed semen instrument or cytometer
132 detection laser
134 beam expansion
136 first detection laser lens assembly
138 flow cell
140 sample flow stream
142 second detection laser lens assembly
144 avalanche photodiode (APD)
146 data acquisition (DAQ) board
148 kill laser/kill beam
150 kill laser lens assembly
152 analog voltage output signal
154 control box (CBX) interface board
156 FPGA (field programmable gate array) of the control box (CBX) interface board
158 first peak
160 second peak
162 start of the event
164 background
166 background threshold value
168 valley
170 sample point
172 analog to digital converter (ADC) sample rate
174 general purpose processor (GPP)/digital signal processor (DSP)
176 analog to digital (ADC) tracker state machine
178 IDLE (background) state
180 RISING state
182 PEAK state
184 FALLING state
186 VALLEY state
188 low pass filter (LPF)
190 analog to digital converter (ADC)
192 FPGA (field programmable gate array) of the digital acquisition (DAQ) board
194 digital to analog converter (DAC) buffer
196 physical layer (PHY)
198 digital to analog converter (DAC) voltage reference (VREF)
200 non-transitory computer readable medium The present disclosure is not to be limited to the particular embodiments described herein. The following claims set forth a number of the embodiments of the present disclosure with greater particularity.

What is claimed is:

1. A method to discriminate an undesired cell in a multi-cell fluorescent event comprising:
   detecting a fluorescence of at least two cells physically spaced close enough such that the at least two cells create one fluorescent event;
   classifying each cell as an undesired cell or a desired cell based on the detection of the fluorescence of the at least two cells;
   allowing each desired cell to pass; and
   acting on each undesired cell.

2. The method of claim 1, wherein said acting on each undesired cell involves mechanical sorting, fluid switching, acoustic-assisted hydrodynamic focusing, photonic pressure, electrolysis or electroporation, or laser ablation.

3. The method of claim 1 further comprising firing a kill beam with the kill laser to destroy each undesired cell.

4. The method of claim 1 further comprising creating a sample flow by allowing a sheath fluid to enter a semen sexing instrument.

5. A sexed semen product formed as the result of executing the method of any one of claims 1, 2, 3 or 4.

6. The method of claim 1 further comprising introducing cell dye into the at least two cells.

7. The method of claim 1 further comprising exciting the at least two cells with a detection laser or a light emitting diode to cause the fluorescence.

8. The method of claim 1 further comprising collecting each desired cell.

9. The method of claim 1 wherein the fluorescence of the cell determines the sex of the at least two cells.

10. The method of claim 1 further comprising measuring a purity percentage associated with a population of cells.

11. A method of selecting which undesired cell to destroy in a multi-cell fluorescent event comprising:
   detecting a fluorescence of at least two cells physically spaced close enough such that the at least two cells create one fluorescent event;
   converting photons detected in the fluorescence of the at least two cells into an analog voltage output signal;
   identifying a first peak in the analog voltage output signal and associating the first peak with a first cell;
   identifying a second peak in the analog voltage output signal and associating the second peak with a second cell;
   measuring an amplitude of the first peak and an amplitude of the second peak; and
   defaulting a kill laser to fire a kill beam at any cells having an amplitude less than an amplitude of another cell.

12. The method of claim 11 further comprising:
   defining a dead cell threshold percentage or an adjustable fixed value;
   determining the difference between the amplitude of the first peak and the amplitude of the second peak;
   determining if the difference between the amplitude of the first peak and the amplitude of the second peak is greater than the dead cell threshold percentage or the adjustable fixed value; and
   configuring the kill laser to override the defaulting step and to fire at any cells having an amplitude higher than an amplitude of another cell if the difference is greater than the dead cell threshold percentage or the adjustable fixed value.

13. The method of claim 11 further comprising filtering and digitizing the analog voltage output signal.

14. A sexed semen product formed as the result of executing the method of any one of claims 11, 12 or 13.

15. A sexed semen system comprising:
   a source of sperm cells;
   a detection laser capable of exciting a sperm cell;
   a fluorescence detector;
   a computer processing unit for determining the sex of the sperm cell based on an output of the fluorescence detector;
   an analog to digital converter (ADC) which converts an analog voltage output signal from the fluorescence detector into a digital output signal;
   a field programmable gate array (FPGA) receiving the digital output, the FPGA having an ADC state tracker machine which monitors a raw ADC value of the analog voltage output signal to determine if a multi-cell fluorescent event has occurred, and if so, to classify each sperm cell as desirable or undesirable; and
   a kill laser for destroying an undesirable sperm cell.

16. The system of claim 15 wherein the source of sperm cells comprises a sheath fluid encapsulating the sperm cells.

17. The system of claim 15 wherein the fluorescence detector is an avalanche photodiode (APD) sensor.

18. The system of claim 15 wherein the ADC tracker state machine includes an IDLE state, a RISING state, a PEAK state, a FALLING state, and a VALLEY state.

19. The system of claim 15 further comprising a general purpose processor (GPP) or a digital signal processor (DSP) using a defined gate to generate a fire signal to the FPGA with the option of the FPGA to make a kill decision based on the defined gate.

20. The system of claim 15 further comprising a low pass filter for passing signals with a frequency lower than a selected cutoff frequency.

* * * * *